(12) United States Patent
Yokoyama

(10) Patent No.: US 11,246,620 B2
(45) Date of Patent: Feb. 15, 2022

(54) ULTRASONIC SURGICAL INSTRUMENT

(71) Applicant: OLYMPUS CORPORATION, Hachioji (JP)

(72) Inventor: Ken Yokoyama, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 267 days.

(21) Appl. No.: 16/394,362

(22) Filed: Apr. 25, 2019

(65) Prior Publication Data

US 2019/0247080 A1 Aug. 15, 2019

Related U.S. Application Data

(63) Continuation of application No. PCT/JP2016/082182, filed on Oct. 28, 2016.

(51) Int. Cl.
*A61B 17/32* (2006.01)
*A61B 17/16* (2006.01)

(52) U.S. Cl.
CPC ...... *A61B 17/320068* (2013.01); *A61B 17/16* (2013.01); *A61B 17/1615* (2013.01);
(Continued)

(58) Field of Classification Search
CPC ........... A61B 17/320068; A61B 2017/320069; A61B 2017/32007; A61B 2017/320071;
(Continued)

(56) References Cited

U.S. PATENT DOCUMENTS

2001/0004695 A1* 6/2001 Vercellotti ........... A61C 8/0092
606/79
2006/0195107 A1* 8/2006 Jones ................. A61B 17/1644
606/79
(Continued)

FOREIGN PATENT DOCUMENTS

JP H5-309098 A 11/1993
JP H06-14934 A 1/1994
(Continued)

OTHER PUBLICATIONS

May 26, 2020 Office Action issued in Japanese Patent Application No. 2018-547056.
(Continued)

*Primary Examiner* — Matthew J Lawson
*Assistant Examiner* — Lisa Nguyen
(74) *Attorney, Agent, or Firm* — Oliff PLC

(57) ABSTRACT

An ultrasonic surgical instrument for boring a hole in a femur, including: an ultrasonic vibrator capable of generating ultrasonic vibration; a probe including a proximal end portion connected with the ultrasonic vibrator and a distal end treatment portion capable of boring a bone hole in the femur, and transmitting the ultrasonic vibration; and a cylindrical member covering the proximal end portion of the probe and not covering an exposed portion including the distal end treatment portion. The distal end treatment portion includes a columnar portion having a cross-sectional area that is larger than that of a remainder of the exposed portion of the probe.

20 Claims, 12 Drawing Sheets

(52) U.S. Cl.
    CPC ...... *A61B 17/1664* (2013.01); *A61B 17/1675* (2013.01); *A61B 17/32* (2013.01); *A61B 17/320016* (2013.01); *A61B 2017/32007* (2017.08); *A61B 2017/32009* (2017.08); *A61B 2017/320073* (2017.08)

(58) Field of Classification Search
    CPC ....... A61B 2017/320072; A61B 2017/320073; A61B 2017/320074; A61B 2017/320075; A61B 2017/320077; A61B 2017/320084
    See application file for complete search history.

(56) References Cited

U.S. PATENT DOCUMENTS

| | | | |
|---|---|---|---|
| 2006/0235305 A1* | 10/2006 | Cotter | A61B 17/1604 600/459 |
| 2010/0167235 A1 | 7/2010 | Vercellotti et al. | |
| 2015/0150565 A1 | 6/2015 | Huwais | |
| 2016/0151647 A1 | 6/2016 | Onuma et al. | |
| 2016/0157884 A1 | 6/2016 | Onuma et al. | |

FOREIGN PATENT DOCUMENTS

| | | |
|---|---|---|
| JP | 2015-534898 A | 12/2015 |
| WO | 2015/045199 A1 | 4/2015 |
| WO | 2015/045438 A1 | 4/2015 |
| WO | 2016/111051 A1 | 7/2016 |
| WO | 2016/111052 A1 | 7/2016 |
| WO | 2016/132835 A1 | 8/2016 |

OTHER PUBLICATIONS

Apr. 30, 2019 International Preliminary Report on Patentability issued in International Application No. PCT/JP2016/082182.

Jan. 31, 2017 International Search Report issued in International Patent Application No. PCT/JP2016/082182.

\* cited by examiner

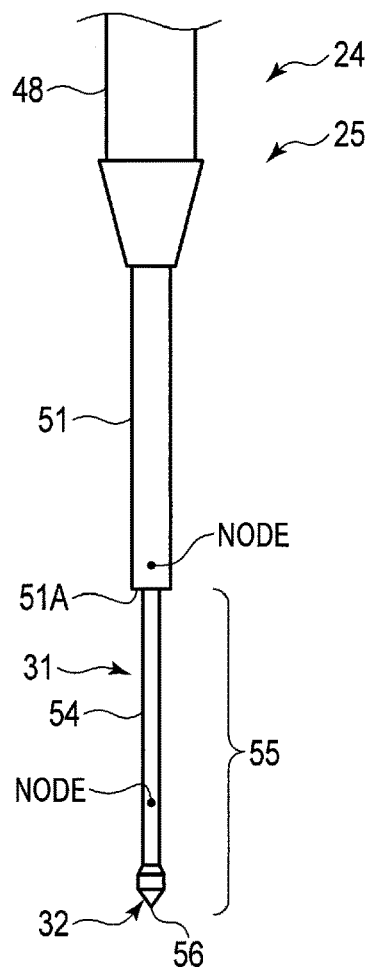
F I G. 3
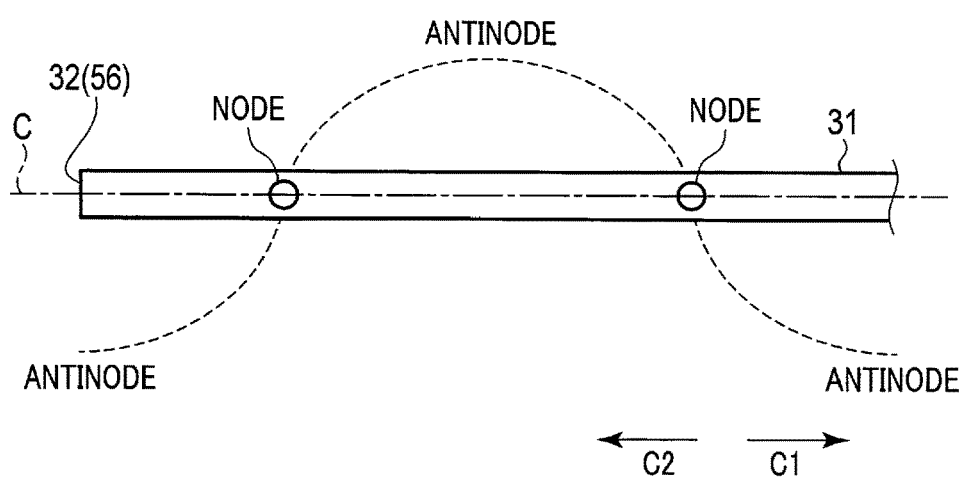
F I G. 4

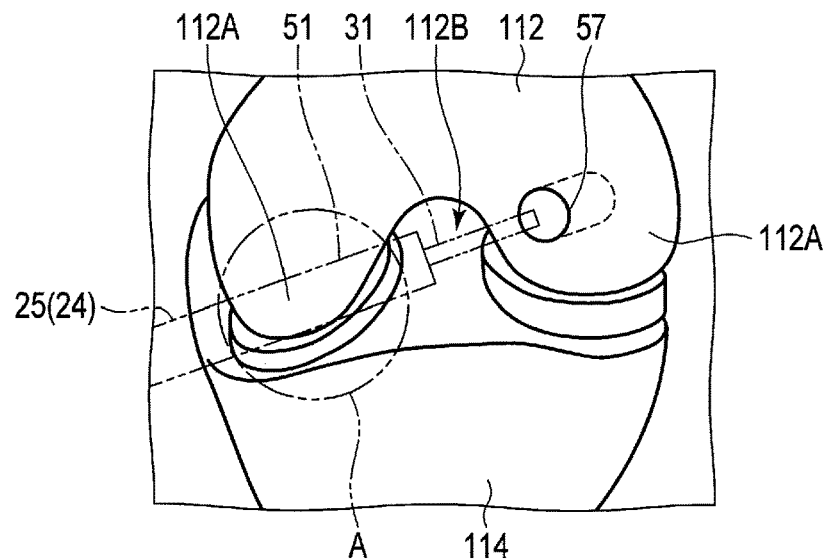
F I G. 5
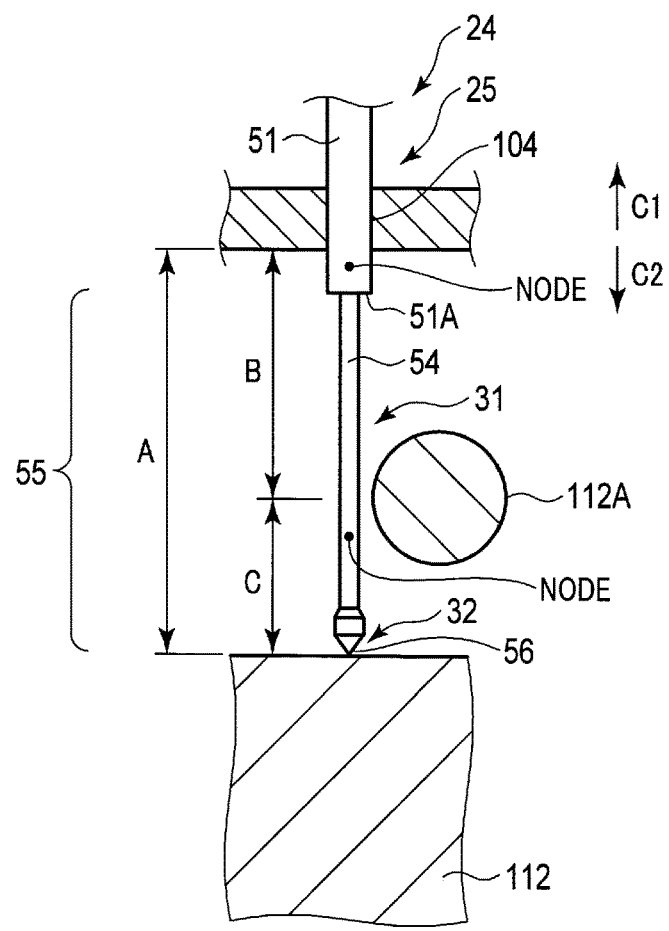
F I G. 6

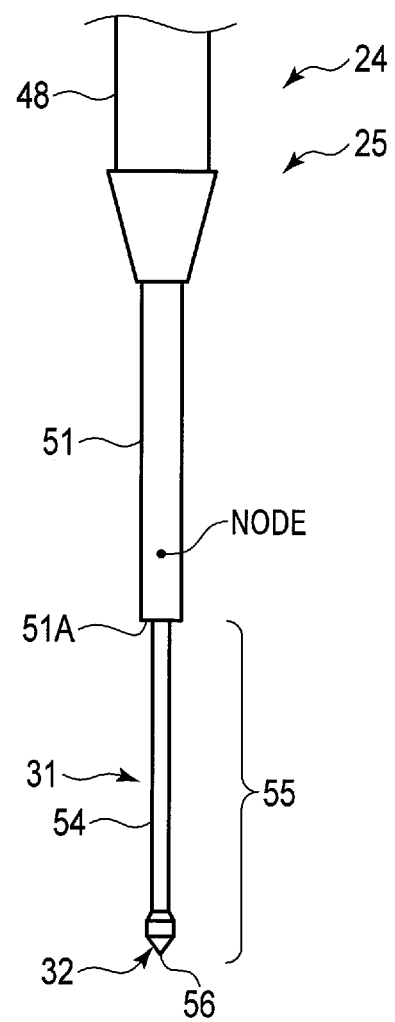
F I G. 8

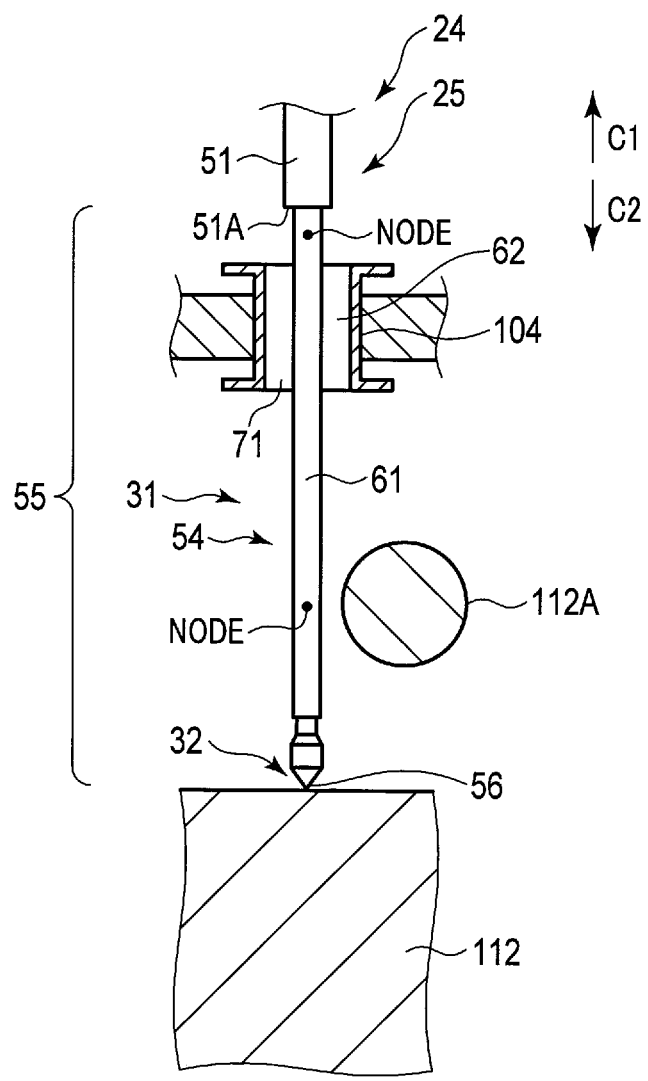
F I G. 11

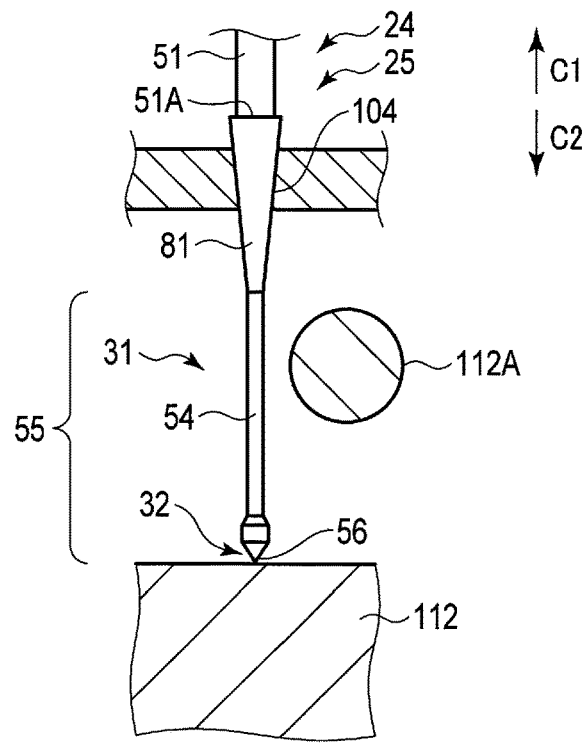
F I G. 16
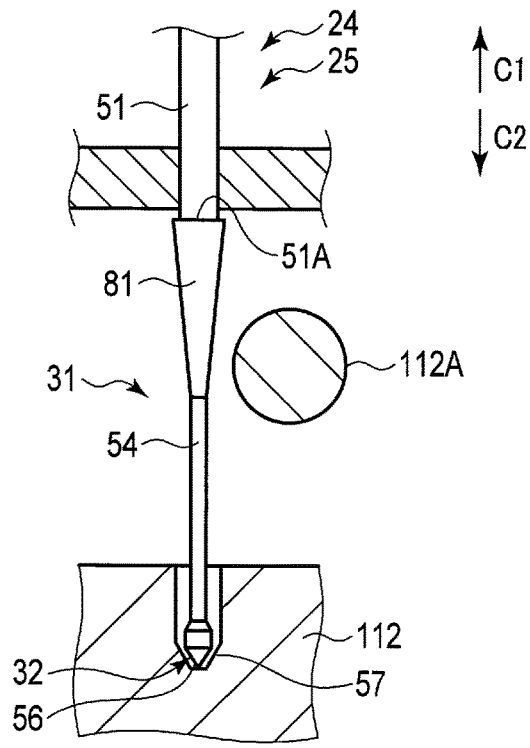
F I G. 17

ULTRASONIC SURGICAL INSTRUMENT

This application is a Continuation Application of PCT Application No. PCT/JP2016/082182, filed Oct. 28, 2016, the entire contents of all of which are incorporated herein by reference.

BACKGROUND

The present disclosure relates to an ultrasonic surgical instrument to treat a biotissue, such as bones.

For example, US20100167235A1 discloses a surgical tool to bore a hole in the bone. The surgical tool functions by ultrasonic waves, and the chip of the tool includes a plurality of cutting elements defining the outline of the hole formed in the bone. Removal (cutting) of the bone is performed with minute vibration by ultrasonic vibration. SUMMARY When the bone or the like in the deep part in the human body is treated using a surgical instrument to treat bones, there are cases where the surgical instrument interferes with the tissue or the bone or the like positioned on the surface layer side of the human body. This generates needs for ultrasonic surgical instruments preventing such interferences.

An ultrasonic surgical instrument to bore a bone hole in the femur according to the embodiment comprises: an ultrasonic vibrator generating ultrasonic vibration; a probe including a proximal end portion connected with the ultrasonic vibrator and a distal end treatment portion boring a bone hole in the femur, and transmitting the ultrasonic vibration; and a cylindrical member covering the probe, the cylindrical member covering the proximal end portion of the probe and including a distal end portion positioned on the proximal end portion side of the distal end treatment portion of the probe at a distance of 25 to 80 mm from the distal end treatment portion.

BRIEF DESCRIPTION OF DRAWINGS

FIG. 3 is a front view illustrating a treatment tool of the treatment system illustrated in FIG. 2;

FIG. 4 is a schematic diagram illustrating amplitude in a state where a probe of the treatment tool illustrated in FIG. 3 is vibrated with ultrasonic waves at 40 to 50 kHz, and schematically illustrating node positions and abdominal positions;

FIG. 5 is a schematic diagram illustrating a state in which the probe interferes with a femur medial condyle when a recessed hole is formed in the femur using a conventional ultrasonic probe;

FIG. 6 is a cross-sectional view illustrating a state in which cutting of the femur is started using the treatment tool illustrated in FIG. 3;

FIG. 8 is a front view illustrating the treatment tool of the treatment system according to an exemplary embodiment;

FIG. 11 is a cross-sectional view illustrating a state of starting cutting of the femur using the treatment unit illustrated in FIG. 9;

FIG. 16 is a cross-sectional view illustrating a state of starting cutting of the femur using a treatment tool illustrated in FIG. 14 and FIG. 15; and FIG. 17 is a cross-sectional view illustrating a process of forming a recessed hole in the femur using the treatment tool illustrated in FIG. 14 and FIG. 15.

DETAILED DESCRIPTION

An exemplary embodiment will be explained hereinafter with reference to FIG. 1 to FIG. 8. A treatment system according to the present embodiment is suitably used for, for example, an anterior cruciate ligament (ACL) reconstructive operation of the knee joint and other operations.

Figure 1:
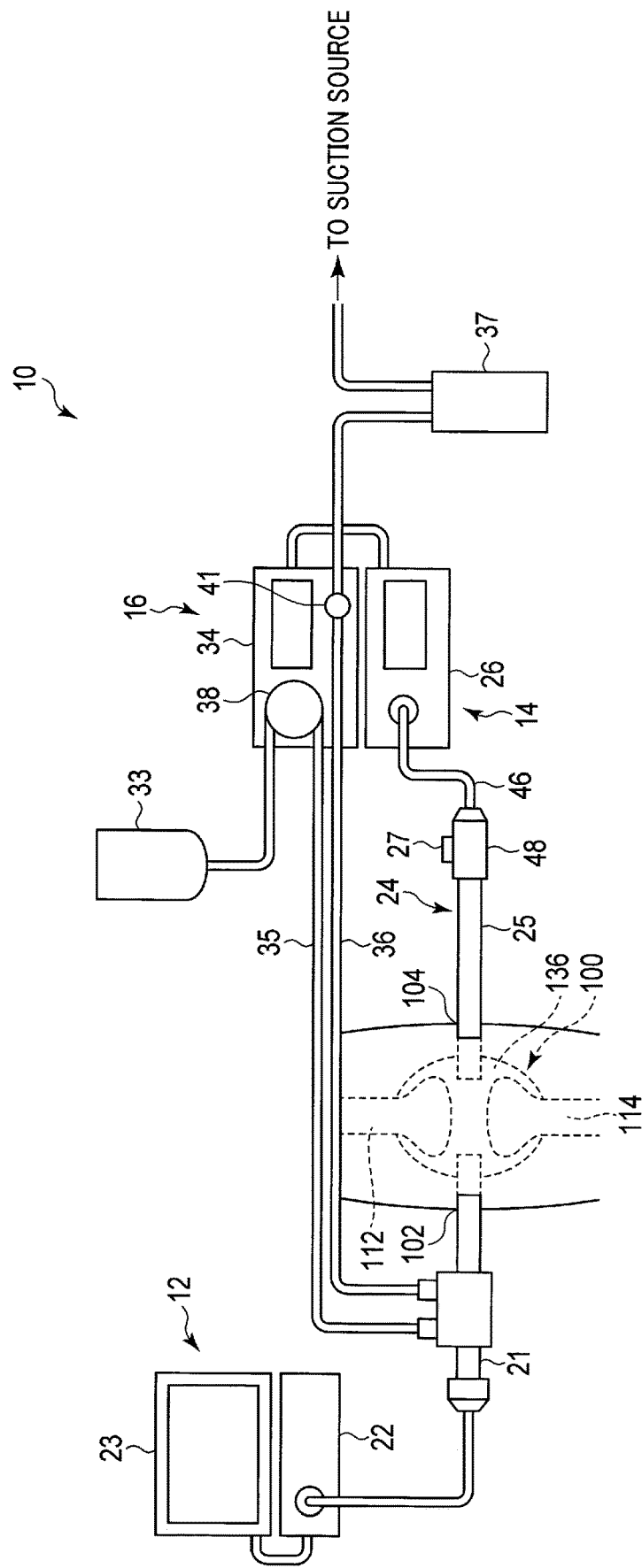
FIG. 1 is a schematic diagram illustrating a treatment system according to an exemplary embodiment.

When a knee joint 100 is treated, for example, a treatment system 10 illustrated in FIG. 1 is used. The treatment system 10 includes an arthroscope device 12, a treatment device 14, and a perfusion device 16.

As illustrated in FIG. 1, the arthroscope device 12 includes an arthroscope 21 observing the inside of the knee joint 100, that is, the inside of an articular cavity 136, an arthroscope controller 22 performing image processing on the basis of a subject image imaged with the arthroscope 21, and a monitor 23 displaying an image generated by image processing performed with the arthroscope controller 22. The arthroscope 21 is inserted into the articular cavity 136 of the knee joint 100 with a first portal 102 serving as a skin incision portion causing the inside of the knee joint 100 and the outside of the skin of the patient to communicate with each other. The position of the first portal 102 is not uniform, but can be properly determined according to the state of the patient. A cannula (not illustrated) is disposed on the first portal 102, and the arthroscope 21 may preferably be inserted into the articular cavity 136 of the knee joint 100 through the cannula. The arthroscope 21 and a treatment tool 24 of the treatment device 14 described later are illustrated in a state of being opposed to each other in FIG. 1, but they are arranged with a proper positional relation according to the position of the treatment target or the like.

The treatment device 14 includes a treatment unit 25, a treatment unit controller 26, and a switch 27. The switch 27 is illustrated as a hand switch in FIG. 1, but may be a foot switch. The treatment device 14 is an example of the ultrasonic surgical instrument.

The processing unit controller 26 supplies proper energy (electric power) to a vibrator unit 28 (described later) of the treatment unit 25 in accordance with an operation of the switch 27, to transmit ultrasonic vibration to a distal end treatment portion 32 of a probe 31 of the treatment unit 25 described later. The probe 31 is inserted into the articular cavity 136 of the knee joint 100 with a second portal 104 serving as a skin incision portion causing the inside of the knee joint 100 and the outside of the skin of the patient to communicate with each other. The position of the second portal 104 is not uniform, but can be properly determined according to the state of the patient. A cannula (not illustrated) is disposed on the second portal 104, and the probe 31 may preferably be inserted into the articular cavity 136 of the knee joint 100 through the cannula. The switch 27 maintains a state in which a vibrator (ultrasonic vibrator) described later is driven in the state in which the switch 27 is pressed, and the state in which the vibrator is driven is released when the switch 27 in the pressed state is released.

This example illustrates the case where one switch 27 is provided, but a plurality of switches 27 may be provided. The amplitude of the vibrator can be properly set with the treatment unit controller 26. For this reason, by the operation of the switch 27, the amplitude may be set different, although the frequency of the ultrasonic vibration output from the vibrator unit 28 described later is the same. Accordingly, the switch 27 may preferably be capable of switching the amplitude of the vibrator unit 28 between a plurality of states, for example, a large amplitude and a small amplitude.

The perfusion device 16 includes a liquid source 33 containing a perfusion liquid, such as a physiological saline solution, a perfusion pump unit 34, a liquid feed tube 35 connected at one end with the liquid source 33, a liquid discharge tube 36, and a suction bottle 37 connected with one end of the liquid discharge tube 36. The suction bottle 37 is connected with a suction source attached to the wall of the operating room. The perfusion pump unit 34 is capable of feeding the perfusion liquid from the liquid source 33 with a liquid feed pump 38. The perfusion pump unit 34 is also capable of switching suction and stop suction of the perfusion liquid in the articular cavity 136 of the knee joint 100 with respect to the suction bottle 37 by opening and closing a pinch valve 41 serving as a liquid discharge valve.

The other end of the liquid feed tube 35 serving as a liquid feed pipe line is connected with the arthroscope 21. For this reason, the perfusion liquid can be fed into the articular cavity 136 of the joint 100 through the arthroscope 21. The other end of the liquid discharge tube 36 serving as a liquid discharge pipe line is connected with the arthroscope 21. This structure enables discharge of the perfusion liquid from the inside of the articular cavity 136 of the joint 100 through the arthroscope 21. As a matter of course, the other end of the liquid discharge tube 36 may be connected with the treatment tool 24 to enable discharge of the perfusion liquid from the inside of the articular cavity 136. The perfusion liquid may be fed and discharged through another portal.

Figure 2:
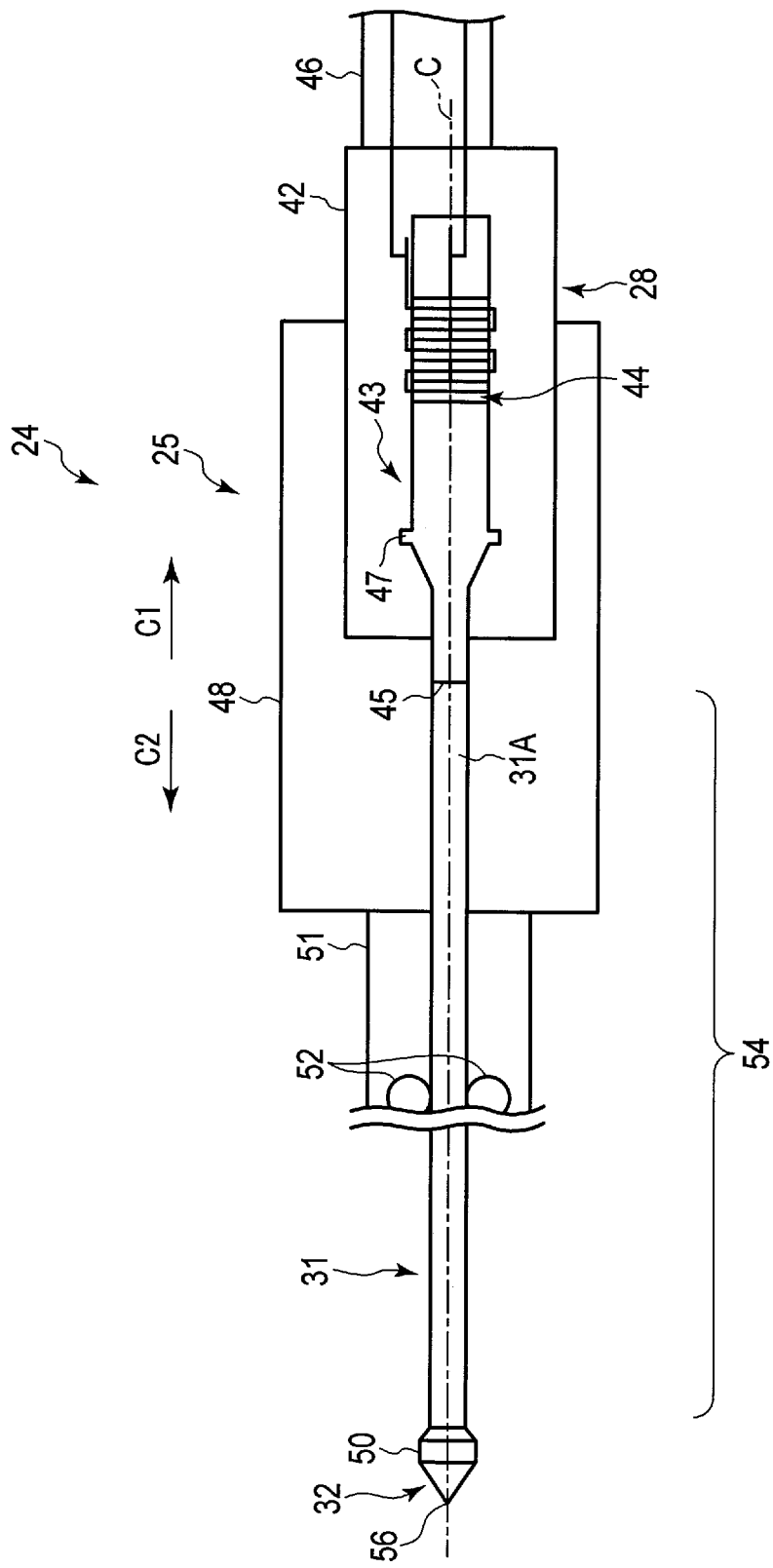
FIG. 2 is a schematic diagram illustrating a treatment unit according to the treatment system illustrated in FIG. 1.

As illustrated in FIG. 2, the treatment unit 25 includes the treatment tool 24 and the vibrator unit 28. It is preferable that the vibrator unit 28 is attachable to and detachable from the treatment tool 24, but the treatment tool 24 may be united with the vibrator unit 28. The vibrator unit 28 includes a vibrator case 42, a horn member 43, a vibrator 44 (ultrasonic vibrator, piezoelectric element) formed of a bolt-clamped Langevin-type transducer, and a connecting portion 45 provided at the distal end of the horn member 43 and connected with a proximal end portion 31A of the probe 31 described later. The connecting unit 45 preferably projects to the distal end side of the vibrator case 42 along a central axis C of the vibrator unit 28. A cable 46 extends from the proximal end of the vibrator case 42 of the vibrator unit 28. One end of the cable 46 is connected with the vibrator unit 28, and the other end of the cable 46 is connected with the treatment unit controller 26. The horn member 43 and the vibrator 44 form a united vibrator. In the present embodiment, the vibrator is set to generate ultrasonic vibration at a certain frequency (for example, 47 kHz) in a specific frequency range (for example, 40 to 50 kHz).

The vibrator case 42 supports a supported portion 47 of the vibrator. Because the vibrator unit 28 is publicly known, a detailed explanation thereof is omitted. In the state in which the vibrator 44 is caused to generate vibration, the connecting portion 45 serves as an antinode of ultrasonic vibration. Although not illustrated in FIG. 2, the switch 27 is preferably disposed in the vibrator case 42 of the vibrator unit 28 or a housing 48 of the treatment tool 24 described later.

The treatment tool 24 includes the housing 48 (handle), a cylindrical member 51 (outer cylinder, sheath) extended from the housing 48 along the central axis C, and the probe 31 (ultrasonic probe) inserted through the inside of the cylindrical member 51. In the treatment tool 24, the side on which the housing 48 is positioned with respect to the cylindrical member 51 is referred to as proximal end side (arrow C1 side), and the side opposite to the proximal end side is referred to as distal end side (arrow C2 side). The cylindrical member 51 is attached to the housing 48 from the distal end C2 side. The cylindrical member 51 covers a part extending from the proximal end side 31A of the probe 31 to a substantially middle portion of the probe 31 with respect to the direction of the central axis C. A watertight rubber lining 52 is provided between the internal circumferential surface of the cylindrical member 51 and the external circumferential surface of the probe 31. The rubber lining 52 prevents the liquid from entering the inside of the cylindrical member 51. The rubber lining 52 is provided to correspond to, for example, the node position of ultrasonic vibration, in the state in which the probe 31 is vibrated with ultrasonic waves at a certain frequency (for example, 47 kHz) in a specific frequency range (for example, 40 to 50 kHz).

The housing 48 of the treatment tool 24 is formed of a material having electrical insulation property. The vibrator case 42 of the vibrator unit 28 is detachably connected with the housing 48. The housing 48 of the treatment tool 24 may be preferably united with the vibrator case 42 of the vibrator unit 28.

A rotary knob (not illustrated) serving as a rotary operating member may be attached to the housing 48 of the treatment tool 24. The rotary knob is rotatable with respect to the housing 48 around the central axis of the cylindrical member 51. The housing 48, the cylindrical member 51, the distal end treatment portion 32 described later, and a probe main member unit 54 of the vibrator unit 28 rotate together with respect to the housing 48 around the central axis C of the probe main member unit 54 by rotation of the rotary knob.

The external circumferential surfaces of the housing 48 and the cylindrical member 51 of the treatment tool 24 have insulating property, but may have no insulating property. The probe 31 is formed of a material capable of transmitting ultrasonic vibration, such as a metal material. An exemplary metal material includes a titanium alloy material. The whole length of the probe 31 is, for example, preferably substantially an integral multiple of a half wavelength based on the resonant frequency of the vibrator 44. The whole length of the probe 31 is not limited to an integral multiple of a half wavelength based on the resonant frequency of the vibrator 44, but properly regulated according to the material and/or the amplitude extension ratio or the like. For this reason, the whole length of the probe 31 may be substantially an integral multiple of a half wavelength based on the resonant frequency of the vibrator 44.

Figure 10:
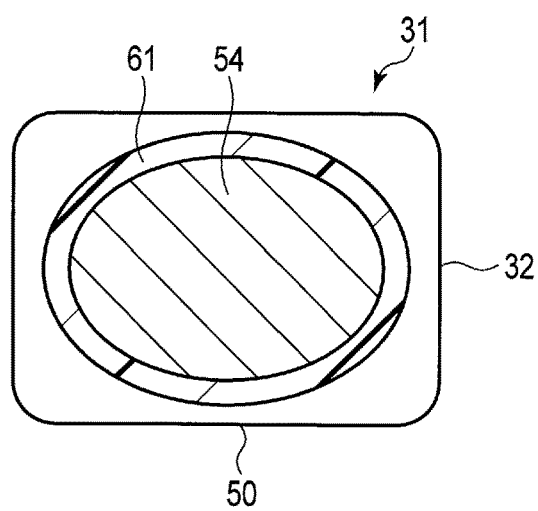
FIG. 10 is a cross-sectional view illustrating the treatment unit illustrated in FIG. 9 and cut in a position of line F10-F10.

As illustrated in FIG. 2 and FIG. 3, the probe 31 includes the probe main member unit 54, the proximal end portion 31A provided on the probe main member unit 54 and connected with the ultrasonic vibrator 44, and the distal end treatment portion 32 provided on the distal end C2 side of the probe main member unit 54, and capable of boring a hole in the bone serving as the treatment target by ultrasonic vibration. The probe main member unit 54 has, for example, a substantially cylindrical shape. The probe main member unit 54 may has an oval cross section, as illustrated in FIG. 10. The probe main member unit 54 includes a portion exposed from the cylindrical member 51 and a portion contained in the cylindrical member 51. As illustrated in FIG. 3, the distal end treatment portion 32 and a portion exposed from the cylindrical member 51 in the probe main member unit 54 form an exposed portion 55.

In the present embodiment, a distal end portion 51A of the cylindrical member 51 is positioned on the proximal end portion 31A side of the distal end treatment portion 32 (cutting portion 56) of the probe 31 at a distance of 25 to 80 mm from the distal end treatment portion 32. In other words, the length of the exposed portion 55 in the central axis C direction is 25 to 80 mm. More preferably, the length of the exposed portion 55 in the central axis C direction is 40 to 80 mm (the distal end portion 51A of the cylindrical member 51 is positioned on the proximal end portion 31A side of the distal end treatment portion 32 (cutting portion 56) of the probe 31 at a distance of 40 to 80 mm therefrom). More preferably, the length of the exposed portion 55 in the central axis C direction is 50 to 80 mm (the distal end portion 51A of the cylindrical member 51 is positioned on the proximal end portion 31A side of the distal end treatment portion 32 (cutting portion 56) of the probe 31 at a distance of 50 to 80 mm therefrom).

Ultrasonic vibration generated with the ultrasonic vibrator 44 is transmitted to the probe main member unit 54 through the connecting portion 45 of the vibrator. Ultrasonic vibration generated with the vibrator 44 is transmitted to the distal end treatment portion 32 through the connecting portion 45 and the probe main member unit 54.

The distal end treatment portion 32 includes the cutting portion 56 (cutting blade) at a distal end thereof. In this example, the cutting portion 56 is formed as a square pyramid illustrated in FIG. 2 and FIG. 3. The projection shape of the cutting portion 56 when the proximal end C1 side is viewed from the distal end C2 side along the central axis C (longitudinal axis) of the distal end treatment portion 32 has a substantially square shape illustrated with a solid line in FIG. 9, or a polygonal shape. The polygon may be an equilateral polygon. The cutting portion 56 has a small contact area with the bone in the initial state of cutting the bone. This structure enables concentration of pressure (stress) in the distal end of the cutting portion 56, and enables start of cutting with relatively small force.

From the viewpoint of reducing friction between the femur 112 and the distal end treatment portion 32 and the viewpoint of discharging the excised piece generated from the femur 112, the maximum external shape portion of the distal end treatment portion 32 in the direction (ultrasonic vibration direction) along the central axis C preferably has a short length. For this reason, a columnar portion 50 (see FIG. 2) having a square cross-sectional shape in the distal end treatment portion 32 is preferably configured to have a cross section gradually decreasing along the central axis C, not the same shape or the same cross section.

It is preferable that the probe 31 is moved straight along the central axis C, to form a recessed hole 57 straight along the central axis C with the columnar portion 50 of the distal end treatment portion 32. For this reason, to prevent staggering of the distal end treatment portion 32 and form the recessed hole 57 straight, the columnar portion 50 is required to have a certain length in the central axis C direction.

In addition, the distal end treatment portion 32 cuts the femur 112 while ultrasonic vibration of a proper amplitude is transmitted to the probe 31. For this reason, the columnar portion 50 of the distal end treatment portion 32 is required to have proper strength. In the case where the cross section of the columnar portion 50 gradually decreases from the distal end toward the proximal end side of the distal end treatment portion 32, a certain cross-section decrease ratio or the like may cause difficulty in forming the distal end treatment portion 32 with strength necessary for cutting the femur 112 with the distal end treatment portion 32, while ultrasonic vibration of proper amplitude to the probe 31.

The columnar portion 50 (see FIG. 2) of the distal end treatment portion 32 of the probe 31 according to the present embodiment includes a region forming the maximum external shape portion with a certain length along the central axis C. In the present embodiment, the cross section of a surface of the columnar portion 50 orthogonal to the central axis C is the same or substantially the same in the central axis C direction. As described above, because the distal end treatment portion 32 is provided with the columnar portion 50, it is possible to form the straight recessed hole 57 in the same shape as the maximum external shape portion of the columnar portion 50 in cutting of the femur 112, while the strength of the distal end treatment portion 32 is maintained when the probe 31 is moved straight along the central axis C toward the distal end side.

When the ACL reconstructive operation is performed using a STG tendon described later, the external shape of the cross section orthogonal to the longitudinal axis of the grafted tendon is formed in a substantially rectangular shape of a size of approximately 4 mm×5 mm. For this reason, as an example, when the projection shape of the distal end treatment portion 32 is a substantially rectangular shape, the external shape of the cross section orthogonal to the central axis C preferably has a size of approximately 4 mm×5 mm.

As schematically illustrated in FIG. 4, in the state in which the probe 31 is vibrated with ultrasonic waves at, for example, a certain frequency (for example, 47 kHz) in a specific frequency range (for example, 40 to 50 kHz) an antinode position, a node position, an antinode position, and a node position . . . alternately appear from the distal end (cutting portion 56) of the distal end treatment portion 32 to the proximal end portion 31A of the probe 31. In addition, a node of ultrasonic vibration appears in the exposed portion 55 of the probe 31. Ultrasonic vibration transmitted to the probe 31 is longitudinal vibration along the central axis C direction of the probe 31. The sine curve illustrated in FIG. 4 schematically illustrates amplitude in each point on the probe 31. The portion at which the amplitude is maximum is an antinode position, and the portion at which the amplitude is zero is a node position. The wavelength $\lambda$ can be calculated from the following expression.

$$\lambda = C/f = \sqrt{E/\rho}/f \qquad \text{[Numerical Expression 1]}$$

In the expression described above, C is transmission speed in the medium, f is the frequency, E is Young's modulus, and p is density. Each of E and p is material physical property, and the internode distance (λ/2) depends on the material and the frequency. The length from the distal end (distal end of the cutting portion 56) of the probe 31 to the node position is approximately λ/4 from FIG. 4, and may be finely regulated in consideration of the strength of the distal end treatment portion 32, the stability of vibration, and the accessibility to the treatment target region.

In the present embodiment, as illustrated in FIG. 3, in the state where the probe 31 is vibrated (resonated) by ultrasonic waves at a certain frequency (for example, 47 kHz) in a specific frequency range (for example, 40 to 50 kHz), the node position appears in at least two positions, that is, the middle position in the exposed portion 55 and a position covered with the cylindrical member 51. For example, in the case of using medical titanium alloy as the material of the probe 31, the distance (λ/2) between the node positions of ultrasonic vibration in the ultrasonic-vibrated state is approximately 47 mm (in the case at 50 kHz) to 53 mm (in the case at 40 kHz) when it is calculated with the expression of Numerical Expression 1 described above.

The probe main member unit 54 is preferably formed in a straight shape. The distal end treatment portion 32 is preferably extended straight from the distal end of the probe main member unit 54 toward the distal end side, but may be properly bent in consideration of the visibility of the distal end treatment portion 32 with the arthroscope 21. For this reason, the longitudinal axis of the distal end treatment portion 32 may agree with the central axis C of the probe main member unit 54, or may be different therefrom.

Figure 7:
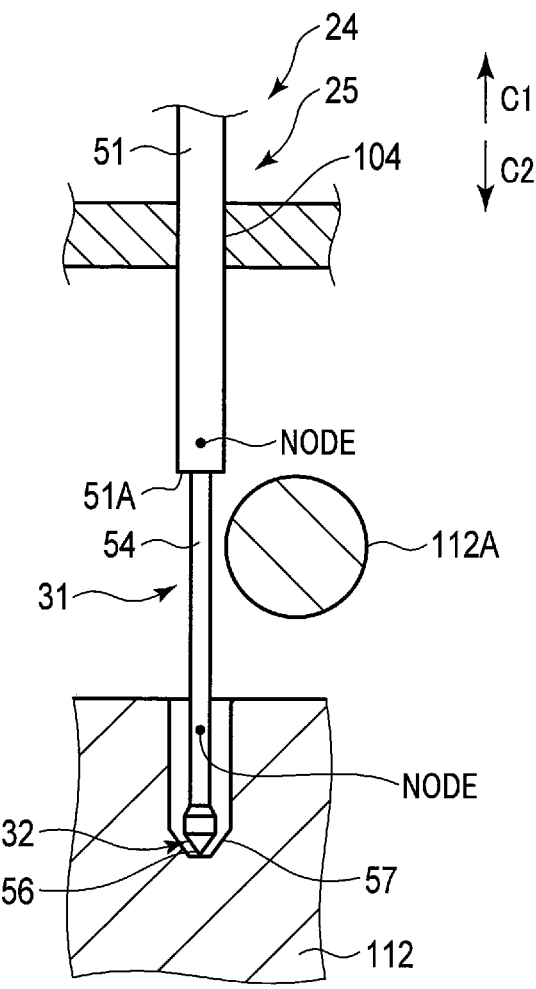
FIG. 7 is a cross-sectional view illustrating a process of forming a recessed hole using the treatment tool illustrated in FIG. 3.

The following is an explanation of the function of the treatment system 10 according to the present embodiment with reference to FIG. 5 to FIG. 7, with an example of the case of performing an anterior cruciate ligament (ACL) reconstructive operation of the knee joint. The explanation hereinafter mainly illustrates the case of forming the recessed hole 57 in the bone 112 using the treatment unit.

The operating method can be divided into, for example, two, according to the material of the grafted tendon of the ligament to be reconstructed. One is a method of using a semitendinosus tendon or a gracilis tendon inside the knee as the grafted tendon (STG tendon). The other is a method of using a patellar tendon as the grafted tendon (BTB tendon). The following example illustrates the case of using a STG tendon as an example to form the bone hole by an inside-out method going from the inside of the articular cavity 136 toward the outside of the femur 112.

In the method of using a STG tendon as the grafted tendon, a semitendinosus tendon or a gracilis tendon located inside the knee is extracted as the grafted tendon (STG tendon) from the patient's body. The length of the tendon at this operation is approximately 250 mm to 300 mm. The extracted tendon is bent a plurality of times, such as four to six times, to form a grafted tendon having a rectangular cross section orthogonal to the longitudinal axis and provided with a substantially rectangular external shape.

By contrast, a prepared hole of a small diameter is formed in a predetermined position of the femur 112 using a drill or the like to pierce the femur 112, and a prepared hole of a small diameter is formed in a predetermined position a tibia 114 using a drill or the like to pierce the tibia 114. The prepared hole may be performed in a state in which a perfusion liquid, such as a physiological saline solution, is circulated in the articular cavity 136.

As illustrated in FIG. 6, a recessed hole 57 (bone hole) is formed from the inside of the articular cavity 136 using the treatment system 10 according to the present embodiment such that the recessed hole 57 is concentric with the center of the prepared hole of the femur 112 (in the drawings attached to the present specification, illustration of the prepared hole is omitted). No prepared hole may be provided in some operating methods. The diameter of the recessed hole 57 is larger than the diameter of the prepared hole. Formation of the recessed hole 57 is also performed in the state in which a perfusion liquid, such as a physiological saline solution, is circulated in the articular cavity 136. In the case of using a STG tendon, the recessed hole 57 has a rectangular shape, for example, with shorter sides of 4 mm, longer sides of 5 mm, and a depth of approximately 15 mm.

When the switch 27 is operated, energy is supplied from the treatment unit controller 26 to the vibrator 44 of the vibration member fixed on the proximal end portion 31A of the probe 31, and ultrasonic vibration is generated in the vibrator 44. In this manner, ultrasonic vibration is transmitted to the ultrasonic probe 31 through the vibration member (horn member 43). The vibration is transmitted from the proximal end C1 side to the distal end C2 side of the probe 31.

Because the distal end treatment portion 32 serves as an antinode of vibration, the distal end treatment portion 32 is displaced along the central axis C at speed (for example, several thousand m/s). For this reason, when the distal end treatment portion 32 (cutting portion 56) in the state in which vibration is transmitted is pressed against the bone 112 along the central axis C toward the distal end C2 side, the part of the bone 112 which the distal end treatment portion 32 contacts is crushed. Accordingly, as illustrated in FIG. 6 and FIG. 7, a recessed hole 57 is formed in the bone 112 along the central axis C of the distal end treatment portion 32 of the probe 31. In a conventional ultrasonic surgical tool, as illustrated in FIG. 5, when the recessed hole 57 is formed, the cylindrical member 51 interferes with the femur medial condyle 112A at a position illustrated with A in FIG. 5, and the interference may hinder the work of forming the recessed hole 57.

As illustrated in FIG. 6, a distance A from the second portal 104 to the position at which the recessed hole 57 is formed on the femur 112 is generally approximately 70 mm, although it differs between individuals. A distance B from the second portal 104 to a femur medial condyle 112A is generally approximately 40 mm, although it differs between individuals. A distance C from the femur medial condyle 112A to the position at which the recessed hole 57 is formed is generally approximately 30 mm, although it differs between individuals. When the patient is small or a child, each of the sizes described above may be smaller than the values described above.

In the present embodiment, as illustrated in FIG. 6 and FIG. 7, the cylindrical member 51 retreats toward the proximal end C1 side, and the exposed portion 55 is sufficiently long. Specifically, the length of the exposed portion 55 in the central axis C direction is 25 to 80 mm, preferably 40 to 80 mm, more preferably 50 to 80 mm. For this reason, when the length of the exposed portion 55 is, for example, 40 to 80 mm or 50 to 80 mm, a space of at least approximately 10 mm (when the length of the exposed portion 55 is 40 to 80 mm) to 20 mm (when the length of the exposed portion 55 is 50 to 80 mm) is secured between the femur medial condyle 112A and the distal end portion 51A of the cylindrical member 51, even when the distal end treatment portion 32 reaches the position at which the recessed hole 57 is formed in the femur 112. By contrast, even when the length of the exposed portion 55 is 25 to 80 mm, when the patient is small or a child, a space is secured between the femur medial condyle 112A and the distal end portion 51A of the cylindrical member 51, even when the distal end treatment portion 32 reaches the position at which the recessed hole 57 is formed in the femur 112.

For this reason, the cylindrical member 51 does not interfere with the femur medial condyle 112A in the form of the probe 31. The treatment device 14 of the present embodiment enables treatment of removal and cutting even for peripheral tissues (such as the cartilage) around the bones 112 and 114. This structure enables the operator to perform efficient treatment without changing the treatment devices 14 according to the tissue serving as the treatment target. Debris generated when the bone 112 and the cartilage are crushed are properly discharged to the probe main member unit 54 side, and discharged to the outside of the body by flow of the perfusion liquid. When the depth of the recessed hole 57 reaches a predetermined value, preparation of the recessed hole 57 is finished.

By contrast, string is fixed at one end of the grafted tendon. In an example of the anterior cruciate ligament reconstructive operation, a string is inserted through the prepared hole on the femur 112 side, and fixed on the external circumferential portion of the femur 112 around the outlet of the prepared hole with a suspensory fixing tool. In this operation, part of the grafted tendon is inserted into the recessed hole 57, and fixed in close contact with the internal circumferential surface of the recessed hole 57. The other end opposite to one end of the grafted tendon is inserted through the prepared hole formed in the tibia 114, and fixed on the external circumferential surface of the tibia 114 around the outlet of the prepared hole with a tendon-fixing staple. In this manner, the anterior cruciate ligament reconstructive operation is finished.

According to the present embodiment, the ultrasonic surgical instrument is an ultrasonic surgical instrument to form a bone hole in the femur 112, comprising an ultrasonic vibrator generating ultrasonic vibration, the probe 31 including the proximal end portion 31A connected with the ultrasonic vibrator and the distal end treatment portion 32 forming a bone hole in the femur 112 and transmitting the ultrasonic vibration, and the cylindrical member 51 covering the probe 31. The cylindrical member 51 covers the proximal end portion 31A of the probe 31, and includes the distal end portion 51A disposed on the proximal end 31A side of the distal end treatment portion 32 of the probe 31 at a distance of 25 to 80 mm from the distal end treatment portion 32.

When the probe 31 is vibrated with ultrasonic waves at a certain frequency in a specific frequency range, at least one node position of the ultrasonic vibration appears in the exposed portion 55 of the probe 31 located in a position falling out of the cylindrical member 51.

Generally, the diameter of the cylindrical member 51 is larger than the diameter of the probe 31. For this reason, a conventional ultrasonic surgical tool has the possibility that the cylindrical member 51 interferes with the femur medial condyle 112A when a bone hole is formed in the femur 112 and the interference hinders the operation. With the structure described above, the exposed portion 55 of the probe 31 is provided with sufficient length such that the probe 31 projects at a distance of 25 to 80 mm from the distal end portion 51A of the cylindrical member 51 or a node position appears in the exposed portion 55 of the probe 31 (that is, the length from the distal end of the probe 31 to the distal end of the cylindrical member 51 is at least $\lambda/4$ or more). This structure markedly reduces the possibility of interference of the cylindrical member 51 with the femur medial condyle 112A when the bone hole is formed in the femur 112. This structure enables the operator to smoothly perform treatment to form a bone hole in the femur 112 with the sufficiently long probe 31.

The distal end portion 51A of the cylindrical member 51 is positioned on the proximal end portion 31A side of the distal end treatment portion 32 at a distance of 40 to 80 mm from the distal end treatment portion 32. This structure secures, for the exposed portion 55 of the probe 31, a length sufficiently longer than 30 mm being an average length between the position at which the bone hole is formed in the femur 112 and the femur medial condyle 112A. This structure markedly reduces the possibility of interference of the cylindrical member 51 with the femur medial condyle 112A when the bone hole is formed in the femur 112.

The distal end portion 51A of the cylindrical member 51 is positioned on the proximal end portion 31A side of the distal end treatment portion 32 at a distance of 50 to 80 mm from the distal end treatment portion 32. This structure secures, for the exposed portion 55 of the probe 31, a length sufficiently longer than 30 mm being an average length between the position at which the bone hole is formed in the femur 112 and the femur medial condyle 112A. This structure markedly reduces the possibility of interference of the cylindrical member 51 with the femur medial condyle 112A when the bone hole is formed in the femur 112.

The following is an explanation of another exemplary embodiment. In the following discussion, aspects of this embodiment that are different from the embodiment described above will be mainly explained, and an explanation or illustration of aspects that are the same as those of the embodiment described above is omitted.

In the embodiment illustrated in FIG. 8, the vibrator unit 28 is different in output from the vibrator unit 28 according to the embodiment described above. Specifically, the vibrator 44 (bolt-clamped Langevin-type transducer) of the vibrator unit 28 according to the present embodiment is capable of vibrating the distal end treatment portion 32 of the probe 31 by ultrasonic waves at 20 to 25 kHz in a state where the vibrator 44 is connected with the probe 31. When the probe 31 is vibrated with ultrasonic waves as described above at a frequency lower than that of the above embodiment, the node position of ultrasonic vibration appears inside the cylindrical portion 51. For example, when a medical titanium alloy is used as the material of the probe 31, a distance ($\lambda/2$) between the node positions of ultrasonic vibration in the ultrasonic-vibrated state is approximately 90 mm (in the case of 20 kHz) to 120 mm (in the case of 25 kHz) when the distance is calculated with the expression of Numerical Expression 1. Ultrasonic vibration of such a frequency also enables smooth formation of the recessed hole 57 in the femur 112.

The following is an explanation of another exemplary embodiment of the treatment system with reference to FIGS. 9 to 12. The following explanation mainly illustrates aspects different from the above embodiments, and an explanation or illustration of aspects that are the same as those in the above embodiments is omitted.

Figure 9:
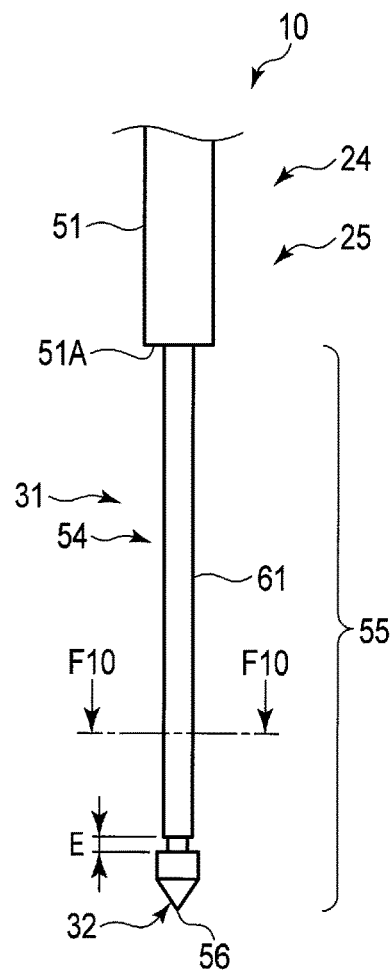
FIG. 9 is a schematic perspective view illustrating a treatment unit of a treatment system according to an exemplary embodiment.

As illustrated in FIG. 9 and FIG. 11, a treatment tool 24 of a treatment system 10 includes a housing 48, a cylindrical member 51 extended from the housing 48 along a central axis C, a probe 31 inserted through the inside of the cylindrical member 51, a protective member 61 covering part of the probe 31, and a second protective member 71 disposed in the second portal 104 serving as the skin incision portion. The protective member 61 is formed of, for example, a synthetic resin material in a cylindrical shape.

The protective member 61 is provided on and in close contact with the external circumferential surface of the probe 31. The protective member 61 enables covering of the probe 31 from the proximal end portion 31A side to a position close to the distal end treatment portion 32 of the probe 31. A space E of several millimeters is provided between the distal end of the protective member 61 and the distal end treatment portion 32. As illustrated in FIG. 11, a space 62 is provided between the protective member 61 and the second protective member 71.

As illustrated in FIG. 9, the distal end treatment portion 32 and a part of a probe main member unit 54 exposed from the cylindrical member 51 form an exposed portion 55. The exposed portion 55 of the probe 31 is formed longer than the exposed portion 55 of the probe 31 of the above embodiments shown in, for example, FIGS. 3, 6, 7, and 8. In the present embodiment, most of the part (shaft portion) of the exposed portion 55 corresponding to the probe main member unit 54 is covered with the protective member 61, instead of being covered with the cylindrical member 51. The length of the exposed portion 55 in the central axis C direction may be, for example, 25 to 80 mm. In addition, in the present embodiment, the exposed portion 55 preferably has a form suitable for forming a recessed hole deeper than the recessed hole 57 formed in the above embodiments or a through hole piercing through the femur 112. For example, the length of the exposed portion 55 in the central axis C direction is preferably 60 to 80 mm.

The protective member 61 is preferably formed of a resin material (heat shrinkable tube) having heat shrinkability. When such probe 31 and protective member 61 are manufactured, in a state in which the heat-shrinkable protective member 61 is disposed around the probe 31, heat treatment is performed on the protective member 61, to bring the protective member 61 in close contact with the external circumferential surface of the probe 31 without a gap. The diameter of the protective member 61 is smaller than the diameter of the cylindrical member 51 and, for example, ½ to ⅓ as large as the diameter of the cylindrical member 51. As is clear from FIG. 10, the diameter (shorter diameter) of the protective member 61 is smaller than the vertical and horizontal lengths of the distal end treatment portion 32. For this reason, the existence of the protective member 61 does not hinder the work in formation of the recessed hole 57.

As illustrated in FIG. 11, in the treatment system 100 of the present embodiment, the second protective member 71 formed of a trocar or the like is preferably disposed in the second portal 104 formed of the skin incision portion. This structure prevents the protective member 61 formed of a heat-shrinkable resin material from directly contacting the skin incision portion.

Figure 12:
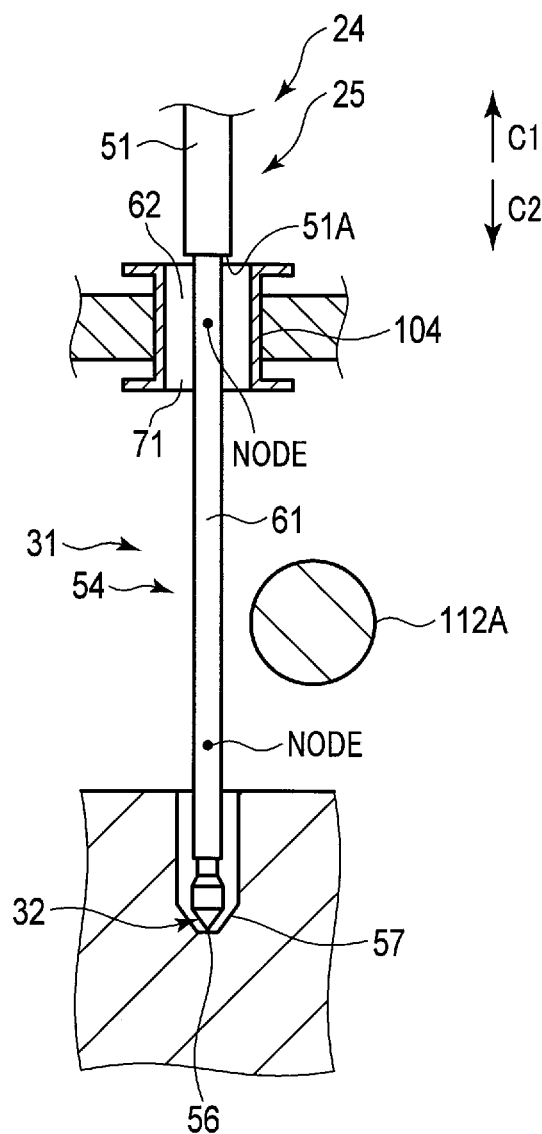
FIG. 12 is a cross-sectional view illustrating a process of forming a recessed hole in the femur using the treatment unit illustrated in FIG. 9.

The following is a function of the treatment system according to the present embodiment with reference to FIG. 11 and FIG. 12, with the case of performing an anterior cruciate ligament reconstructive operation in the knee joint 100 as an example. The explanation mainly illustrates the case of forming a recessed hole 57 in the bone 112 using the treatment unit 25.

In the same manner as the above embodiment, a grafted tendon (STG tendon, BTB tendon) is extracted by a publicly-known method. In parallel with this, a prepared hole of a small diameter is formed in a predetermined position of the femur 112 using a drill or the like to pierce the femur 112, and a prepared hole of a small diameter is formed in a predetermined position of the tibia 114 using a drill or the like to pierce the tibia 114.

A recessed hole 57 is formed from the inside of the articular cavity 136 using the treatment system 10 according to the present embodiment such that the recessed hole 57 is concentric with the center of the prepared hole of the femur 112. The diameter of the recessed hole 57 is larger than the diameter of the prepared hole. No prepared hole may be provided in some operating methods. Formation of the recessed hole 57 is also performed in the state in which a perfusion liquid, such as a physiological saline solution, is circulated in the articular cavity 136. In the case of using a STG tendon, the recessed hole 57 has a rectangular shape, for example, with shorter sides of 4 mm, longer sides of 5 mm, and a depth of approximately 15 mm. In the case of using a BTB tendon, the recessed hole 57 has a rectangular shape, for example, with shorter sides of 5 mm, longer sides of 10 mm, and a depth of approximately 40 mm. As another example, in the treatment with the STG tendon and the BTB tendon, a through hole with a depth of approximately 60 to 70 mm may be formed in the position instead of the recessed hole 57.

When the distal end treatment portion 32 is pressed against the bone 112 in a state in which vibration is transmitted, the part of the bone 112 which the distal end treatment portion 32 contacts is crushed. Accordingly, a recessed hole 57 is formed in the bone 112 along the central axis C of the distal end treatment portion 32 of the probe 31.

In this state, the exposed portion 55 is sufficiently long. Specifically, the length of the exposed portion 55 in the central axis C direction is 60 to 80 mm. For this reason, even when the distal end treatment portion 32 reaches the position in which the recessed hole 57 is formed in the femur 112, a space of approximately 20 to 40 mm is secured between the femur medial condyle 112A and the distal end portion 51A of the cylindrical member 51. With this structure, the cylindrical member 51 does not interfere with the femur medial condyle 112A when the recessed hole 57 is formed. This structure enables formation of the recessed hole 57 sufficiently deep in the femur 112 or a through hole without interference of the cylindrical member 51 with the femur medial condyle 112A. In addition, the probe main member unit 54 is protected with the protective member 61. When the arthroscope 21 is brought into contact with the probe 31 vibrated with ultrasonic waves, the probe 31 may be damaged or the arthroscope 21 may be damaged. In the present embodiment, it is particularly required to insert the probe 31 and the arthroscope 21 into a deep valley-like portion called intercondylar portion 112B (see FIG. 5) between the femur medial condyles 112A to perform treatment. According to the present embodiment, even if the probe 31 vibrating with ultrasonic waves contacts the arthroscope 21 during treatment, the probe 31 or the arthroscope 21 is not damaged, because the protective member 61 protects the probe main member unit 54.

The treatment device 14 according to the present embodiment enables treatment of removal and cutting also for the peripheral tissues (such as the cartilage) around the bone. This structure enables the operator to efficiently perform treatment, without needs for changing the treatment devices 14 in accordance with the tissue serving as the treatment target. Debris generated when the bone and the cartilage are crushed are properly discharged to the probe main member unit 54 side, and discharged to the outside of the body together with the perfusion liquid. When the depth of the recessed hole 57 reaches a predetermined size, preparation of the recessed hole 57 or the through hole is finished.

The method for fixing one end and the other end opposite to one end of the grafted tendon is the same as that of the above embodiment. In this manner, the anterior cruciate ligament reconstructive operation is finished.

According to the present embodiment, the distal end portion of the cylindrical member 51 is positioned on the proximal end portion 31A side of the distal end treatment portion 32 at a distance of 60 to 80 mm from the distal end treatment portion 32. This structure secures, in the exposed portion 55 of the probe 31, a length sufficiently longer than 30 mm serving as an average length between the position in which the bone hole (recessed hole 57) is formed in the femur 112 and the femur medial condyle 112A. This structure markedly reduces the possibility that the cylindrical member 51 interferes with the femur medial condyle 112A when the recessed hole 57 or a through hole is formed in the femur 112.

According to the present embodiment, the ultrasonic surgical instrument includes the protective member 61 covering the probe 31 and in close contact with the probe 31 in the position on the proximal end portion 31A side of the distal end treatment portion 32, and the diameter of the protective member 61 is smaller than the diameter of the cylindrical member 51. With this structure, the probe 31 is covered with the protective member 61 having a diameter smaller than the diameter of the cylindrical member 51. This structure reduces the risk of interference of the probe 31 and the protective member 61 with the femur medial condyle 112A in formation of the recessed hole 57 in the femur 112. In addition, even when the protective member 61 contacts the femur medial condyle 112A, the femur medial condyle 112A is not damaged by the contact, because the surface of the probe 31 is protected with the protective member 61.

In this case, the ultrasonic surgical instrument includes the second protective member 71 interposed between the skin incision portion of the patient and the protective member 61, and the space 62 is provided between the protective member 61 and the second protective member 71. This structure enables heat insulation between the protective member 61 and the second protective member 71 by the air and the like existing in the space 62 between the protective member 61 and the second protective member 71. This structure prevents transmission of heat on the protective member 61 side to the second protective member 71 side, and prevents adverse influence on the tissues existing around the second protective member 71 due to heat.

Figure 13:
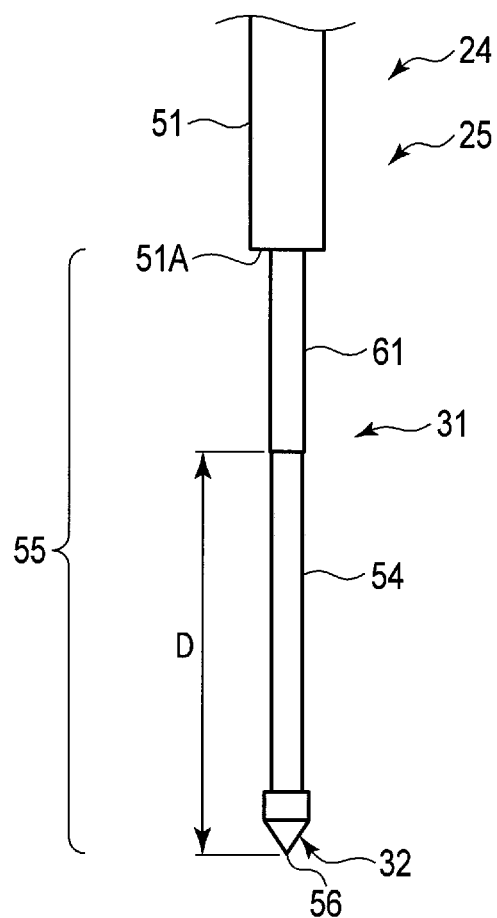
FIG. 13 is a front view illustrating the treatment unit of the treatment system according to an exemplary embodiment.

In another exemplary embodiment of the treatment unit 25 illustrated in FIG. 13, the protective member 61 covers a part extending from the proximal end portion 31A side of the probe 31 to the substantially center portion of the probe main member unit 54. In the exposed portion 55 in a position extending out of the cylindrical member 51, a portion that is not covered with the protective member 61 has a length D of, for example, 40 mm to 50 mm.

For this reason, when the recessed hole 57 is formed in the femur 112 with the probe 31, the portion of the probe 31 corresponding to the femur medial condyle 112a is protected with the protective member 61. With this structure, even when the protective member 61 contacts the femur medial condyle 112A, the femur medial condyle 112A is not damaged by the contact, because the surface of the probe 31 is protected with the protective member 61.

The following is an explanation of another exemplary embodiment of the treatment system 100 with reference to FIG. 14 to FIG. 17. The following explanation mainly illustrates aspects of the present embodiment different from those of the above exemplary embodiments, and an explanation or illustration of aspects that are the same as those in the above embodiments are omitted.

Figure 14:
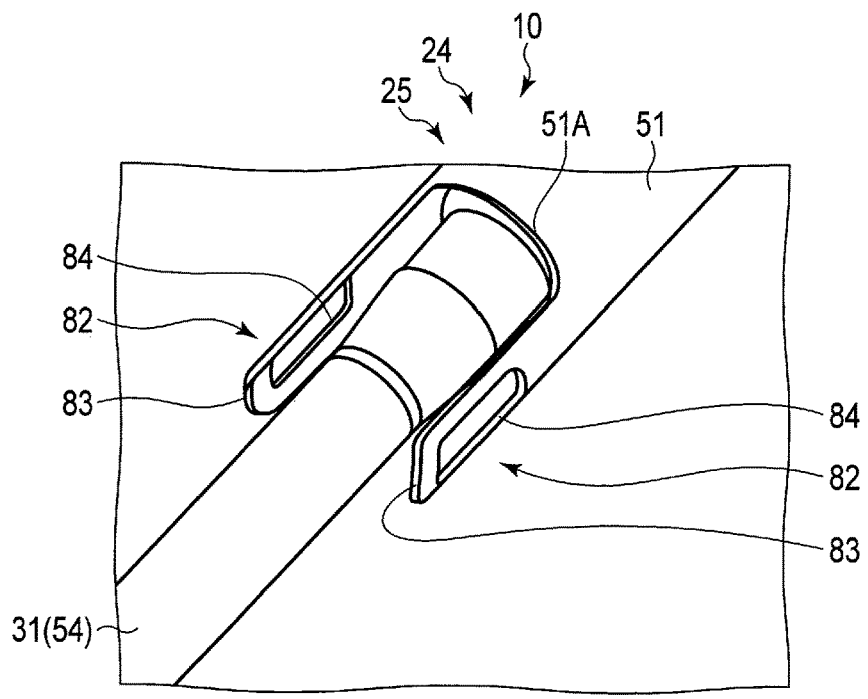
FIG. 14 is a perspective view illustrating a first engaging portion and a probe of a cylindrical member of a treatment unit of a treatment system according to an exemplary embodiment.
Figure 15:
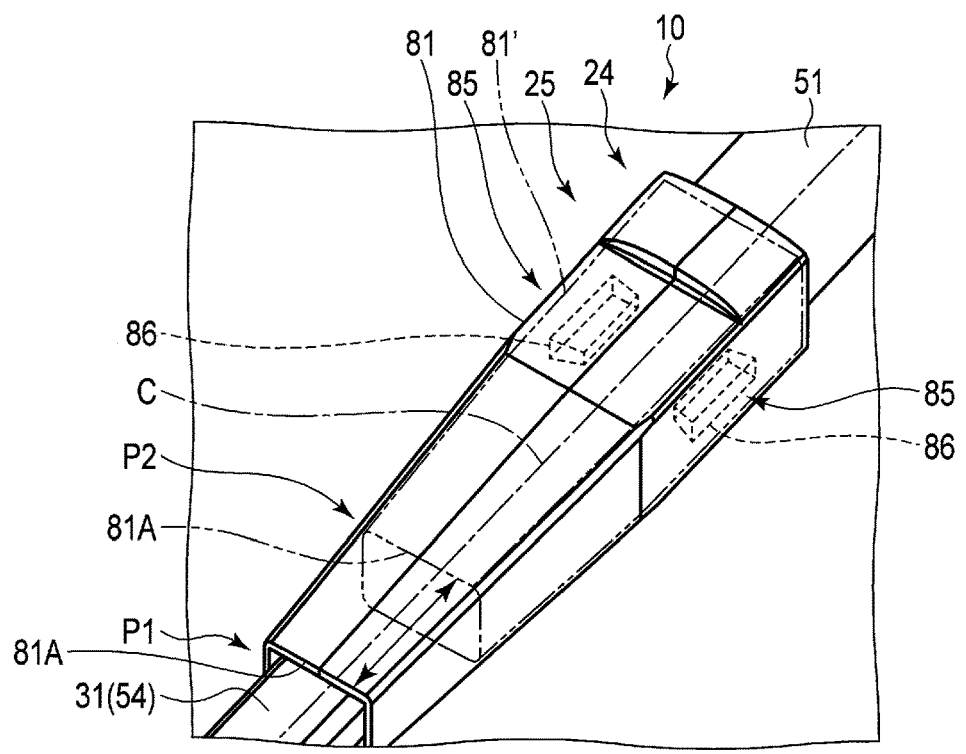
FIG. 15 is a perspective view illustrating an attachment member covering a distal end portion of the cylindrical member in the treatment system according to an exemplary embodiment.

As illustrated in FIG. 14 and FIG. 15, the treatment tool 24 of the treatment system 10 includes a housing 48, a cylindrical member 51 (external cylinder) extended from the housing 48 along the central axis C, a probe 31 inserted through the inside of the cylindrical member 51, and a cylindrical attachment member 81 configured to be attachable to and detachable from a distal end portion 51A of the cylindrical member 51.

As illustrated in FIG. 14, the cylindrical member 51 includes, at the distal end portion 51A, a first engagement portion 82 to fix the attachment member 81. The first engagement portion 82 includes a pair of projecting pieces 83 further projecting from the distal end portion 51A of the cylindrical member 51 toward the distal end C2 side, and a pair of hole portions 84 formed in the respective projecting pieces 83.

As illustrated in FIG. 14 and FIG. 15, the attachment member 81 is attachable to and detachable from the cylindrical member 51 to cover the distal end portion 51A of the cylindrical member 51. The attachment member 81 is formed in a substantially truncated quadrangular pyramid shape having a diameter decreasing toward the distal end treatment portion 32. The attachment member 81 may be formed in a substantially truncated cone shape (tapered shape). The attachment member 81 includes, in an internal surface thereof, a second engagement portion 85 engageable with the first engagement portion 82. The second engagement portion 85 is formed of a pair of hook portions 86 projecting toward the central axis C of the attachment member 81. The hook portions 86 can be fitted into the respective hole portions 84 of the first engagement portion 82, and in this state the attachment member 81 is fixed on the cylindrical member 51. By contrast, the attachment member 81 can be pulled by the user's hand toward the distal end treatment portion 32, and is easily detachable from the cylindrical member 51 as a result of disengagement of the second engagement portion 85 from the first engagement portion 82.

The attachment member 81 may be changed to another attachment member 81' (attachment member illustrated with two-dot chain lines in FIG. 15) having a different length in the central axis C direction. As another example, the attachment member 81 may have a structure in which the distal end portion 81A and therearound are formed in a pleated flexible shape such that the distal end portion 81A is capable of expanding and contracting between a first position P1 (illustrated with solid lines in FIG. 15) and a second position P2 (illustrated with two-dot chain lines in FIG. 15) in the central axis C direction with respect to the cylindrical member 51. These structures enables easy adjustment of the length of the portion of the probe 31 exposed from the attachment member 81 (another attachment member 81') in accordance with the type of treatment or the body size of the patient.

The length of the exposed portion 55 of the probe 31 in the central axis C direction may be equal to that in the embodiment illustrated in FIGS. 3, 6, and 7, or equal to that in the embodiment illustrated in FIGS. 9, 11, and 12.

The following is an explanation of a function of the treatment system 10 according to the present embodiment with reference to FIG. 16 and FIG. 17, with an example of the case of performing an anterior cruciate ligament reconstructive operation in the knee joint 100. This explanation mainly illustrates the case of forming a recessed hole 57 in the bone 112 using the treatment unit 25.

In the same manner as the above embodiments, a grafted tendon (STG tendon, BTB tendon) is extracted by a publicly-known method. In parallel with this, a prepared hole of a small diameter is formed in a predetermined position of the femur 112 using a drill or the like to pierce the femur 112, and a prepared hole of a small diameter is formed in a predetermined position of the tibia 114 using a drill or the like to pierce the tibia 114.

A recessed hole 57 is formed from the inside of the articular cavity 136 using the treatment system 10 according to the present embodiment such that the recessed hole 57 is concentric with the center of the prepared hole of the femur 112. The diameter of the recessed hole 57 is larger than the diameter of the prepared hole. No prepared hole may be provided in some operating methods. Formation of the recessed hole 57 is also performed in the state in which a perfusion liquid, such as a physiological saline solution, is circulated in the articular cavity 136. The values of the shorter sides, the longer sides, and the depth of the recessed hole 57 are equal to those in the case of using the grafted tendon (STG tendon, BTB tendon) according to the embodiment illustrated in FIGS. 9, 11, and 12.

When the distal end treatment portion 32 is pressed against the bone 112 in a state in which vibration is transmitted, the part of the bone 112 which the distal end treatment portion 32 contacts is crushed. Because the attachment member 81 has a diameter decreasing toward the distal end treatment portion 32, the diameter of the attachment member 81 is small in the vicinity of the femur medial condyle 112A. This structure prevents interference of the distal end portion and therearound of the attachment member 81 with the femur medial condyle 112A, and enables the operator to smoothly form the recessed hole 57 in the femur 112. The treatment device 14 of the present embodiment enables treatment of removal and cutting even for peripheral tissues (such as the cartilage) around the bones 112 and 114. This structure enables the operator to perform efficient treatment without changing the treatment devices 14 according to the tissue serving as the treatment target. Debris generated when the bone 112 and the cartilage are crushed are properly discharged to the probe main member unit 54 side, and discharged to the outside of the body together with the perfusion liquid. When the depth of the recessed hole 57 reaches a predetermined value, preparation of the recessed hole 57 is finished.

The method for fixing one end and the other end opposite to one end of the grafted tendon is equal to that of the embodiment illustrated in FIGS. 3, 6, and 7. In this manner, the anterior cruciate ligament reconstructive operation is finished.

According to the present embodiment, the ultrasonic surgical instrument includes the cylindrical attachment member 81 attachable to and detachable from the cylindrical member 51 to cover the distal end portion 51A of the cylindrical member 51. This structure enables protection of the distal end portion 51A of the cylindrical member 51 with the attachment member 81. With this structure, when the recessed hole 57 is formed in the femur 112, even when the distal end portion 51A of the cylindrical member 51 nearly interfere with the femur medial condyle 112A, the attachment member 81 is enabled to abut against the femur medial condyle 112A, instead of the distal end portion 51A of the cylindrical member 51. This structure prevents the risk of damage to the femur medial condyle 112A with the distal end portion 51A of the cylindrical member 51 during treatment.

The diameter of the attachment member 81 decreases toward the distal end treatment portion 32. This structure enables protection of the distal end portion 51A of the cylindrical member 51 by covering the distal end portion 51A with the attachment member 81, and reduces the risk of contact of the cylindrical member 51 itself with the femur medial condyle 112A.

The attachment member 81 is replaceable with another attachment member 81' having a different length in the central axis C direction of the probe 31. As another example, the attachment member 81 is capable of expanding and contracting in the central axis C direction of the probe 31. These structures enable proper fine adjustment of the length of the portion exposed in the probe 31 in accordance with the body size of the patient and/or the type of treatment. This structure improves safety of the operation and user's convenience.

In another exemplary embodiment, a kit may be provided that includes the ultrasonic surgical instrument according to any of the above discussed embodiments, and the interchangeable attachment members 81 and 81'.

Exemplary embodiments have been specifically explained with reference to the drawings. The present disclosure is not limited to the embodiments described above, but includes all implementations performed within a range not departing from the gist of the disclosure.

EXPLANATION OF REFERENCE NUMERALS

10 . . . Treatment System, 12 . . . Arthroscope Device, 14 . . . Treatment Device (Ultrasonic Surgical Instrument), 16 . . . Perfusion Device, 21 . . . arthroscope, 22 . . . arthroscope controller, 23 . . . monitor, 24 . . . treatment tool, 25 . . . treatment unit, 26 . . . treatment unit controller, 27 . . . switch, 28 . . . vibrator unit, 31 . . . Probe, 32 . . . Distal End treatment Portion, 33 . . . liquid source, 34 . . . perfusion pump unit, 35 . . . liquid feed tube, 36 . . . liquid discharge tube, 37 . . . suction bottle, 38 . . . liquid feed pump, 41 . . . pinch valve, 42 vibrator case, 43 . . . horn member, 44 . . . Vibrator, 45 . . . connecting portion, 46 . . . cable, 47 . . . supported portion, 48 . . . housing, 50 . . . columnar portion, 51 . . . Cylindrical Member, 51A . . . Distal End Portion, 52 . . . watertight rubber lining, 54 . . . Probe Main Member Unit, 55 . . . Exposed Portion, 56 . . . cutting portion, 57 . . . Recessed Hole, 61 . . . Protective Member, 62 . . . Space, 71 . . . Second Protective Member, 81 . . . Attachment Member, 81' . . . Another Attachment Member, 102 . . . first portal, 104 . . . second portal, 112 . . . Femur, 112A . . . femur medial condyle, 112B . . . intercondylar portion, 114 . . . tibia, 136 . . . articular cavity.

What is claimed is:

1. An ultrasonic surgical instrument for boring a hole in a femur, comprising:
    an ultrasonic vibrator configured to generate ultrasonic vibration;
    a probe including:
        a proximal end portion connected with the ultrasonic vibrator, and
        a distal end treatment portion configured to bore a bone hole in the femur, and transmit the ultrasonic vibration to the femur, the distal end treatment portion including:
            a cutting portion provided at a distal end thereof, the cutting portion being configured to cut the femur by the ultrasonic vibration; and
            a columnar portion adjacent to the cutting portion; and
    a cylindrical member covering the proximal end portion of the probe and not covering an exposed portion of the probe including the distal end treatment portion, wherein:
the columnar portion has a cross-sectional area orthogonal to a boring direction of the distal end treatment portion that is larger than a cross-sectional area of a remainder of the exposed portion of the probe; and
a distal end of the cylindrical member is proximally spaced from the distal end treatment portion by a distance of 25 to 80 mm.

2. The ultrasonic surgical instrument according to claim 1, wherein the distance between the distal end of the cylindrical member from the distal end treatment portion is 40 to 80 mm.

3. The ultrasonic surgical instrument according to claim 2, wherein the distance between the distal end of the cylindrical member from the distal end treatment portion is 50 to 80 mm.

4. The ultrasonic surgical instrument according to claim 3, wherein the distance between the distal end of the cylindrical member from the distal end treatment portion is 60 to 80 mm.

5. The ultrasonic surgical instrument according to claim 1, wherein a position of at least one node of the ultrasonic vibration is in the exposed portion of the probe extending out of the cylindrical member when the probe is vibrated by ultrasonic waves at a certain frequency.

6. The ultrasonic surgical instrument according to claim 1, further comprising a cylindrical attachment member detachably attached to the cylindrical member and covering a distal end portion of the cylindrical member.

7. The ultrasonic surgical instrument according to claim 6, wherein the attachment member has a diameter that decreases from a proximal end to a distal end of the attachment member in a direction from the cylindrical member toward the distal end treatment portion.

8. The ultrasonic surgical instrument according to claim 6, wherein the attachment member is capable of expanding and contracting in a direction along a central axis of the probe.

9. A kit comprising:
the ultrasonic surgical instrument according to claim 1,
a first cylindrical attachment member detachably attachable to the cylindrical member to cover a distal end portion of the cylindrical member, and
a second cylindrical attachment member that is detachably attachable to the cylindrical member to cover a distal end portion of the cylindrical member, and is interchangeable with the first cylindrical attachment member, the second cylindrical attachment member having a different length in a direction along a central axis of the probe than the first cylindrical attachment member.

10. The ultrasonic surgical instrument according to claim 1, further comprising:
a protective member covering the probe at a position on a proximal end portion side of the distal end treatment portion,
wherein the protective member has a diameter smaller than a diameter of the cylindrical member.

11. The ultrasonic surgical instrument according to claim 10, further comprising:
a second protective member configured to be interposed between a skin incision portion of a patient and the protective member,
wherein the second protective member is spaced from the protective member.

12. The ultrasonic surgical instrument according to claim 10, wherein a cross-sectional area of the probe and the protective member covering the probe is smaller than the cross-sectional area of the columnar portion.

13. A treatment method for boring a hole in a femur via an ultrasonic surgical instrument comprising:
an ultrasonic vibrator configured to generate ultrasonic vibration,
a probe including a proximal end portion connected with the ultrasonic vibrator, and a distal end treatment portion configured to bore a bone hole in the femur, and transmit the ultrasonic vibration to the femur, the distal end treatment portion including a cutting portion that is provided at a distal end thereof and is configured to cut the femur by the ultrasonic vibration, and
a cylindrical member covering the proximal end portion of the probe and not covering an exposed portion of the probe including the distal end treatment portion,
the method comprising:
forming a portal through skin surrounding a knee joint of a patient;
inserting the ultrasonic surgical instrument through the portal;
moving the distal end treatment portion to a position on the femur in which the bone hole is to be formed such that the exposed portion of the probe is positioned between a femur medial condyle and a tibia; and
generating ultrasonic vibration from the ultrasonic vibrator to the distal end treatment portion to bore the bone hole in the femur,
wherein:
the distal end treatment portion comprises a columnar portion that is adjacent to the cutting portion and has a cross-sectional area orthogonal to a boring direction of the distal end treatment portion that is larger than a cross-sectional area of a remainder of the exposed portion of the probe; and
a distal end of the cylindrical member is proximally spaced from the distal end treatment portion by a distance of 25 to 80 mm.

14. The treatment method according to claim 13, further comprising detachably attaching a cylindrical attachment member to a distal end portion of the cylindrical member to cover the distal end portion of the cylindrical member.

15. The treatment method according to claim 14, further comprising adjusting a length of the attachment member along a central axis direction of the probe.

16. The treatment method according to claim 13, wherein:
the ultrasonic surgical instrument further comprises a protective member covering the probe at a position on a proximal end portion side of the distal end treatment portion, and
the protective member has a diameter smaller than a diameter of the cylindrical member.

17. The treatment method according to claim 16, further comprising providing a second protective member in the portal adjacent to a skin incision portion such that the probe and the protective member are inserted through the second protective member,
wherein, when the probe and the protective member are inserted through the second protective member, the protective member is spaced from the second protective member.

18. The treatment method according to claim 16, wherein a cross-sectional area of the probe and the protective member covering the probe is smaller than the cross-sectional area of the columnar portion.

19. The treatment method according to claim 13, wherein a cross-sectional shape of the bone hole orthogonal to the boring direction is identical to a cross-sectional shape of the columnar portion orthogonal to the boring direction.

20. An ultrasonic surgical instrument for boring a hole in a femur, comprising:
- an ultrasonic vibrator configured to generate ultrasonic vibration;
- a probe including:
  - a proximal end portion connected with the ultrasonic vibrator, and
  - a distal end treatment portion configured to bore a bone hole in the femur, and transmit the ultrasonic vibration to the femur, the probe extending along a central axis from the proximal end portion to the distal end treatment portion, the distal end treatment portion including:
    - a cutting portion provided at a distal end thereof, the cutting portion being configured to cut the femur by the ultrasonic vibration; and
    - a columnar portion adjacent to the cutting portion; and
- a cylindrical member covering the proximal end portion and not covering an exposed portion of the probe including the distal end treatment portion and a middle portion that extends in between the columnar portion and the proximal end portion along the central axis,
- wherein the columnar portion has a cross-sectional area orthogonal to a boring direction of the distal end treatment portion that is larger than a cross-sectional area of a remainder of the exposed portion of the probe.

* * * * *